United States Patent
Gupta et al.

(10) Patent No.: US 7,280,862 B2
(45) Date of Patent: Oct. 9, 2007

(54) SYSTEM AND METHOD FOR AUTOMATICALLY OBTAINING A DIGITAL IMAGE OF A HEART

(75) Inventors: Sandeep Narendra Gupta, Hanover, MD (US); Glenn Scott Slavin, Silver Spring, MD (US); Thomas Kwok-Fah Foo, Potomac, MD (US)

(73) Assignee: General Electric Company, Schenectady, NY (US)

( * ) Notice: Subject to any disclaimer, the term of this patent is extended or adjusted under 35 U.S.C. 154(b) by 588 days.

(21) Appl. No.: 10/711,025

(22) Filed: Aug. 18, 2004

(65) Prior Publication Data

US 2006/0058631 A1    Mar. 16, 2006

(51) Int. Cl.
*A61B 5/05*    (2006.01)
*A61B 5/02*    (2006.01)

(52) U.S. Cl. .................. 600/410; 600/425; 600/481; 600/407

(58) Field of Classification Search ................ 600/407, 600/410, 425, 481
See application file for complete search history.

(56) References Cited

U.S. PATENT DOCUMENTS

| | | | | |
|---|---|---|---|---|
| 5,107,838 A | * | 4/1992 | Yamaguchi | 600/410 |
| 6,366,684 B1 | * | 4/2002 | Gerard et al. | 382/132 |
| 6,975,897 B2 | * | 12/2005 | Knoplioch et al. | 600/425 |
| 2002/0156359 A1 | * | 10/2002 | Knoplioch et al. | 600/407 |
| 2005/0033143 A1 | * | 2/2005 | O'Donnell et al. | 600/407 |
| 2005/0113665 A1 | * | 5/2005 | Mohr et al. | 600/407 |
| 2005/0288598 A1 | * | 12/2005 | Lavi et al. | 600/508 |

OTHER PUBLICATIONS

Mullick, R. et al, Automatic Determination of LV Orientation from SPECT Data, Mar. 1995, IEEE Transactions on Medical Imaging, 14[1], pp. 88-99.*
Jackson, Clare et al, Automatic Planning of the Acquisition of Cardiac MR Images, 2003, MICCAI 2003, Springer-Verlag, pp. 541-548.*
Lelieveldt et al.; Automated Observer-Independent Acquisition of Cardiac Short-Axis MR Images: A Pilot Study; Radiology 2001; 221:537-542.
Lelieveldt et al.; Anatomical Model Matching With Fuzzy Implicit Surfaces for Segmentation of Thoracic Volume Scans; IEEE Transactions On Medical Imaging, vol. 18, No. 3, Mar. 1999; 218-230.

* cited by examiner

*Primary Examiner*—Benny Tieu
*Assistant Examiner*—James Talman
(74) *Attorney, Agent, or Firm*—Cantor Colburn LLP

(57) ABSTRACT

A system and a method for obtaining a digital image of a heart of a person are provided. The system scans an internal anatomy of a chest region of the person to obtain scanning data. The system further generates a digital image of four chambers of the heart based on the scanning data.

12 Claims, 8 Drawing Sheets

(Right Ventricle) 100
(Right Atrium) 102
(Left Ventricle) 96
(Left Atrium) 98

110, 106, 94, 104, 112, 108

114

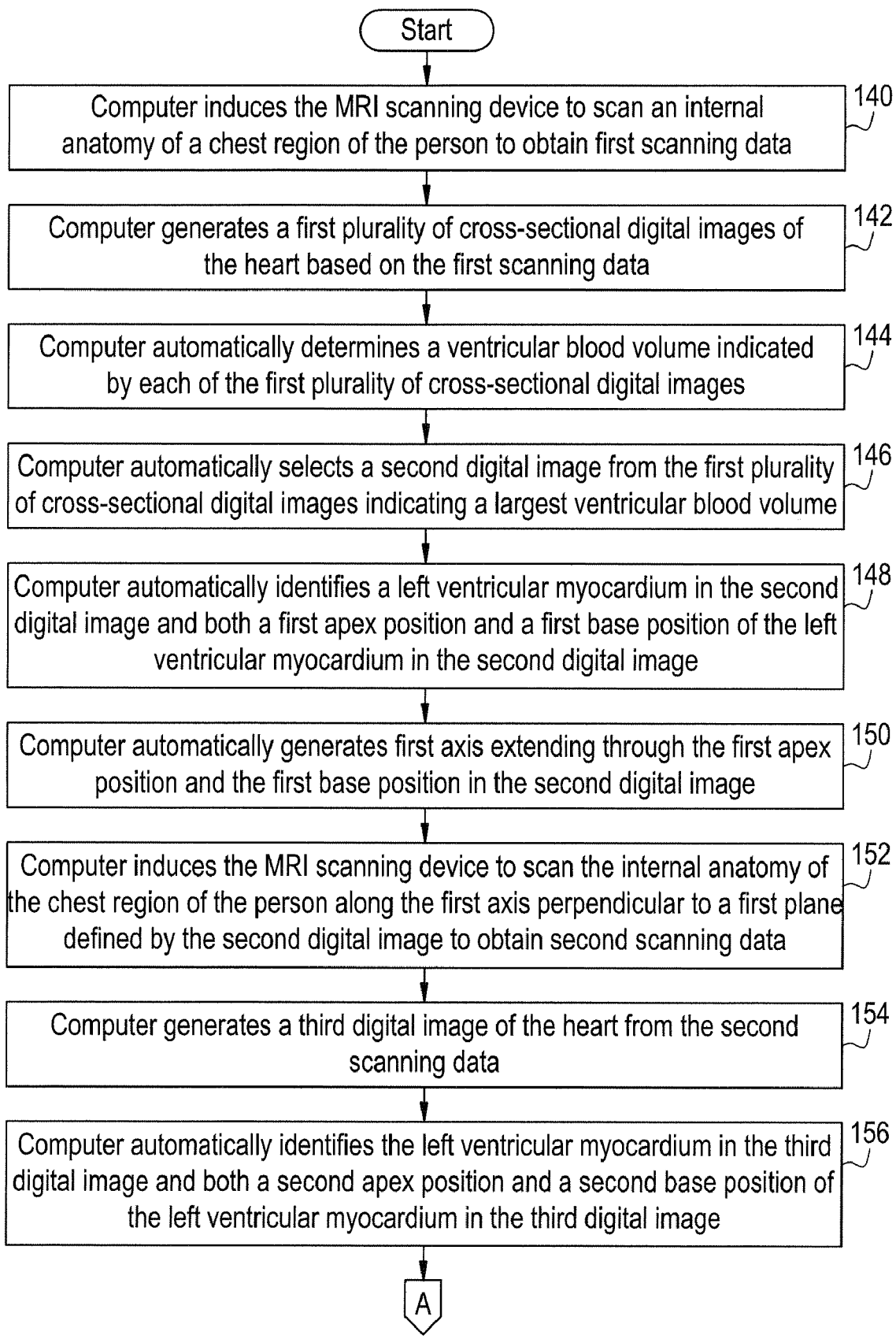

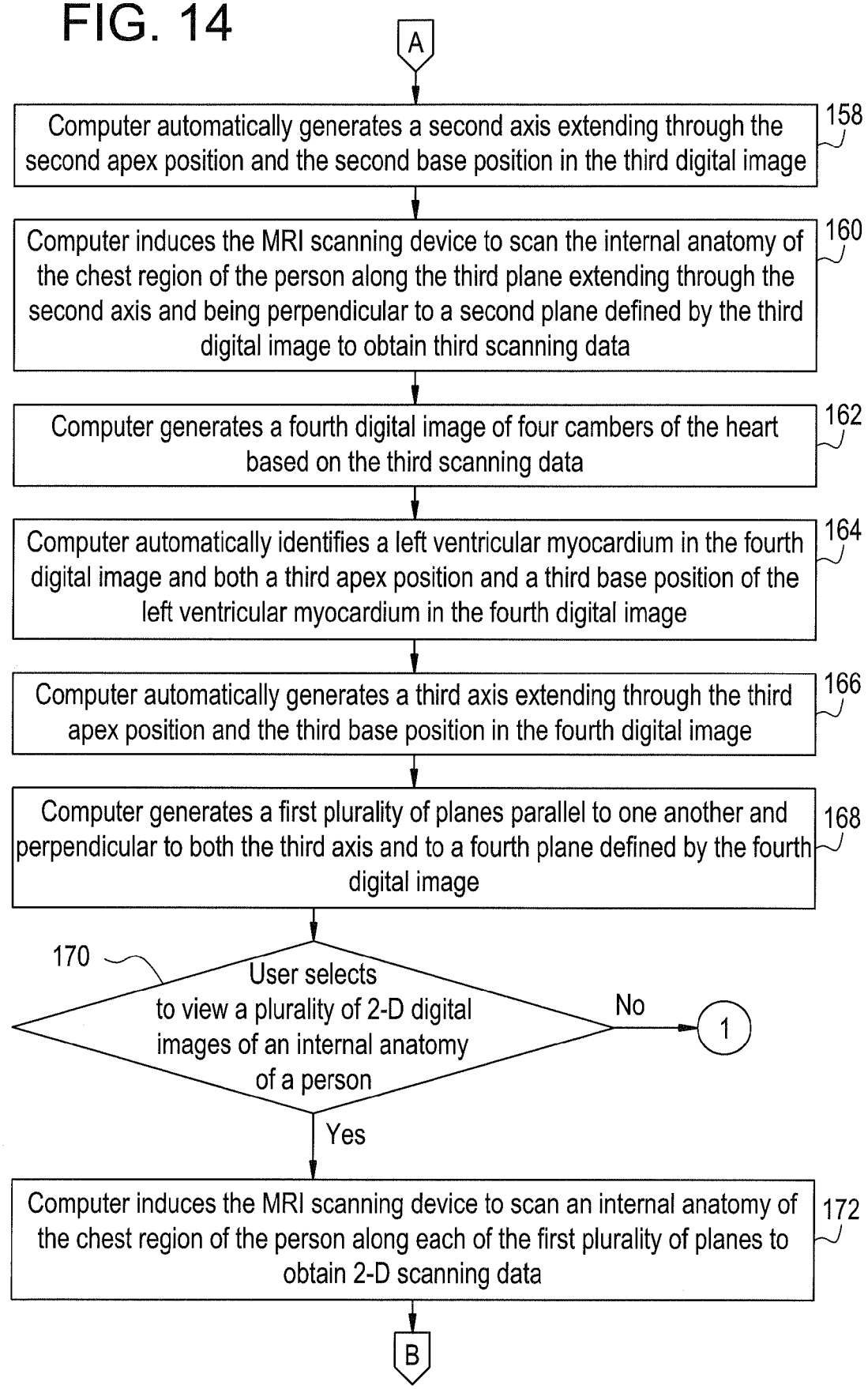

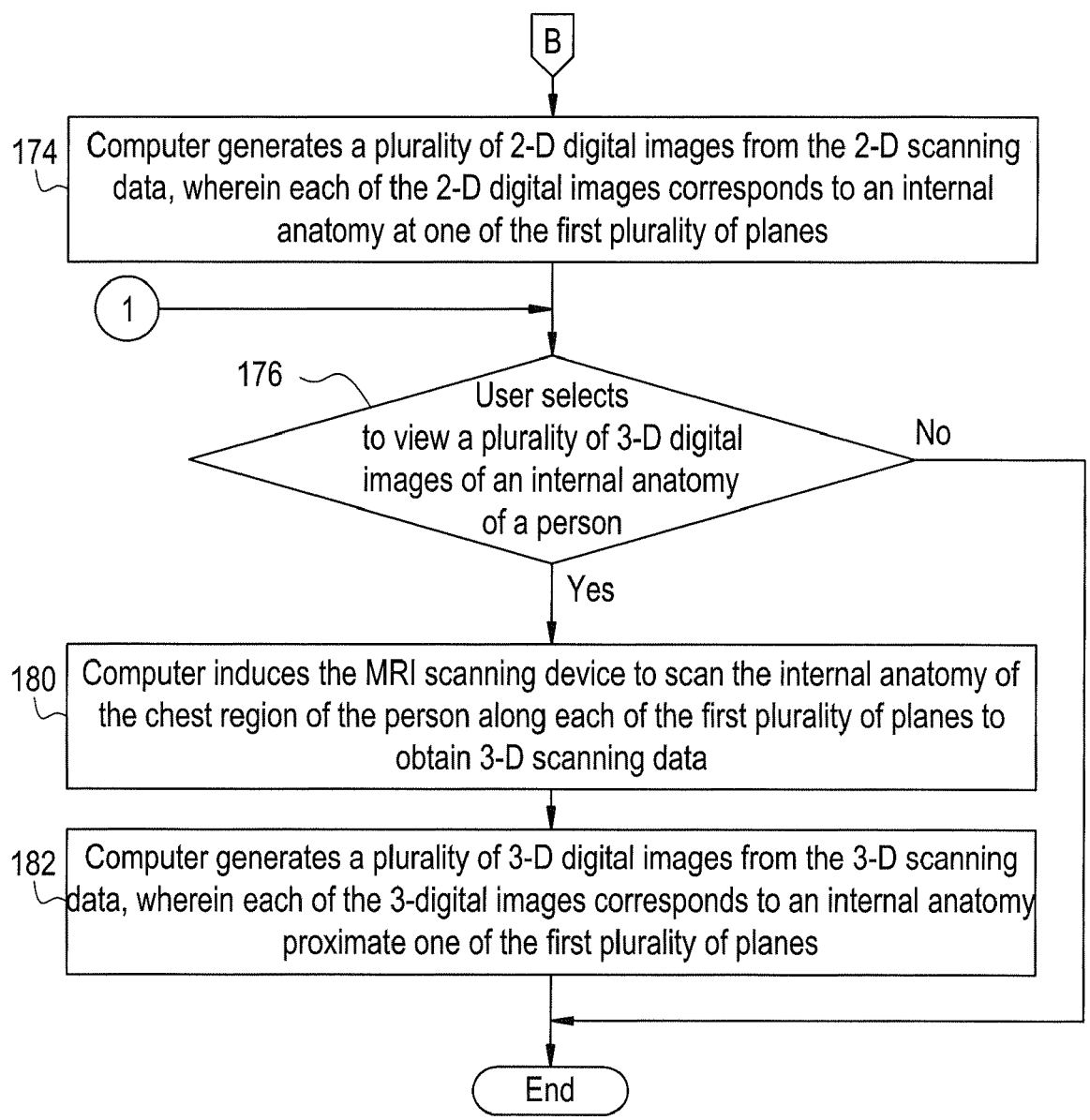

SYSTEM AND METHOD FOR AUTOMATICALLY OBTAINING A DIGITAL IMAGE OF A HEART

BACKGROUND OF INVENTION

MRI devices have been utilized to generate a view of a human heart. Generally, an operator who is familiar with cardiac anatomy provides instructions to an MRI device to define scans that will be taken of the heart. However, two different operators of the MRI device can provide differing scanning instructions to the MRI device when attempting to obtain a desired view, and thereafter obtain differing views of the heart.

Accordingly, the inventors herein have recognized a need for a system and method for automatically obtaining a digital image of the heart.

BRIEF DESCRIPTION OF INVENTION

A method for obtaining a digital image of a heart of a person in accordance with an exemplary embodiment is provided. The method includes scanning an internal anatomy of a chest region of the person to obtain first scanning data. The method further includes generating a first plurality of cross-sectional digital images of the heart based on the first scanning data. The method further includes automatically determining a ventricular blood volume indicated by each of the first plurality of cross-sectional digital images. The method further includes automatically selecting a second digital image from the first plurality of cross-sectional digital images indicating a largest ventricular blood volume. The method further includes automatically identifying a left ventricular myocardium in the second digital image and both a first apex position and a first base position of the left ventricular myocardium in the second digital image. The method further includes automatically generating a first axis extending through the first apex position and the first base position in the second digital image. The method further includes scanning the internal anatomy of the chest region of the person along the first axis perpendicular to a first plane defined by the second digital image to obtain second scanning data. The method further includes generating a third digital image of the heart from the second scanning data. The method further includes automatically identifying the left ventricular myocardium in the third digital image and both a second apex position and a second base position of the left ventricular myocardium in the third digital image. The method further includes automatically generating a second axis extending through the second apex position and the second base position in the third digital image. The method further includes scanning the internal anatomy of the chest region of the person along a third plane extending through the second axis and being perpendicular to a second plane defined by the third digital image to obtain third scanning data. Finally, the method includes generating a fourth digital image of four chambers of the heart based on the third scanning data.

A system for obtaining a digital image of a heart of a person in accordance with another exemplary embodiment is provided. The system includes an MRI scanning device configured to scan an internal anatomy of the person to obtain scanning data. The system further includes a computer operably coupled to the scanning device configured to generate cross-sectional digital images based on the scanning data. The computer is further configured to induce the scanning device to scan the internal anatomy of a chest region of the person to obtain first scanning data. The computer is further configured to generate a first plurality of cross-sectional digital images of the heart based on the first scanning data. The computer is further configured to automatically determine a ventricular blood volume indicated by each of the first plurality of cross-sectional digital images. The computer is further configured to automatically select a second digital image from the first plurality of cross-sectional digital images indicating a largest ventricular blood volume. The computer is further configured to automatically identify a left ventricular myocardium in the second digital image and both a first apex position and a first base position of the left ventricular myocardium in the second digital image. The computer is further configured to automatically generate a first axis extending through the first apex position and the first base position in the second digital image. The computer is further configured to scan the internal anatomy of the chest region of the person along the first axis perpendicular to a first plane defined by the second digital image to obtain second scanning data. The computer is further configured to generate a third digital image of the heart from the second scanning data. The computer is further configured to automatically identify the left ventricular myocardium in the third digital image and both a second apex position and a second base position of the left ventricular myocardium in the third digital image. The computer is further configured to automatically generate a second axis extending through the second apex position and the second base position in the third digital image. The computer is further configured to induce the scanning device to scan the internal anatomy of the chest region of the person along a third plane extending through the second axis and perpendicular to a second plane defined by the third digital image to obtain third scanning data. The computer is further configured to generate a fourth digital image of four chambers of the heart based on the third scanning data.

An article of manufacture in accordance with another exemplary embodiment is provided. The article of manufacture includes a computer storage medium having a computer program encoded therein for obtaining a digital image of a heart of a person. The computer storage medium includes code for scanning an internal anatomy of a chest region of the person to obtain first scanning data. The computer storage medium further includes code for generating a first plurality of cross-sectional digital images of the heart based on the first scanning data. The computer storage medium further includes code for automatically determining a ventricular blood volume indicated by each of the first plurality of cross-sectional digital images. The computer storage medium further includes code for automatically selecting a second digital image from the first plurality of cross-sectional digital images indicating a largest ventricular blood volume. The computer storage medium further includes code for automatically identifying a left ventricular myocardium in the second digital image and both a first apex position and a first base position of the left ventricular myocardium in the second digital image. The computer storage medium further includes code for automatically generating a first axis extending through the first apex position and the first base position in the second digital image. The computer storage medium further includes code for scanning the internal anatomy of the chest region of the person along the first axis perpendicular to a first plane defined by the second digital image to obtain second scanning data. The computer storage medium further includes code for generating a third digital image of the heart from the second scanning data. The computer storage medium further includes code for automatically identifying the left ventricular myocardium in the third digital image and both a second apex position and a second base position of the left ventricular myocardium in the third digital image. The computer storage medium further includes code for automatically generating a second axis extending through the second apex position and the second base position in the third digital image. The computer storage medium further includes code for scanning the internal anatomy of the chest region of the person along a third plane extending through the second axis and perpendicular to a second plane defined by the third digital image to obtain third scanning data. Finally, the computer storage medium includes code for generating a fourth digital image of four chambers of the heart based on the third scanning data.

BRIEF DESCRIPTION OF DRAWINGS

FIGS. 13-15 are flowcharts of a method for automatically obtaining a digital image of the heart.

DETAILED DESCRIPTION

Figure 1:
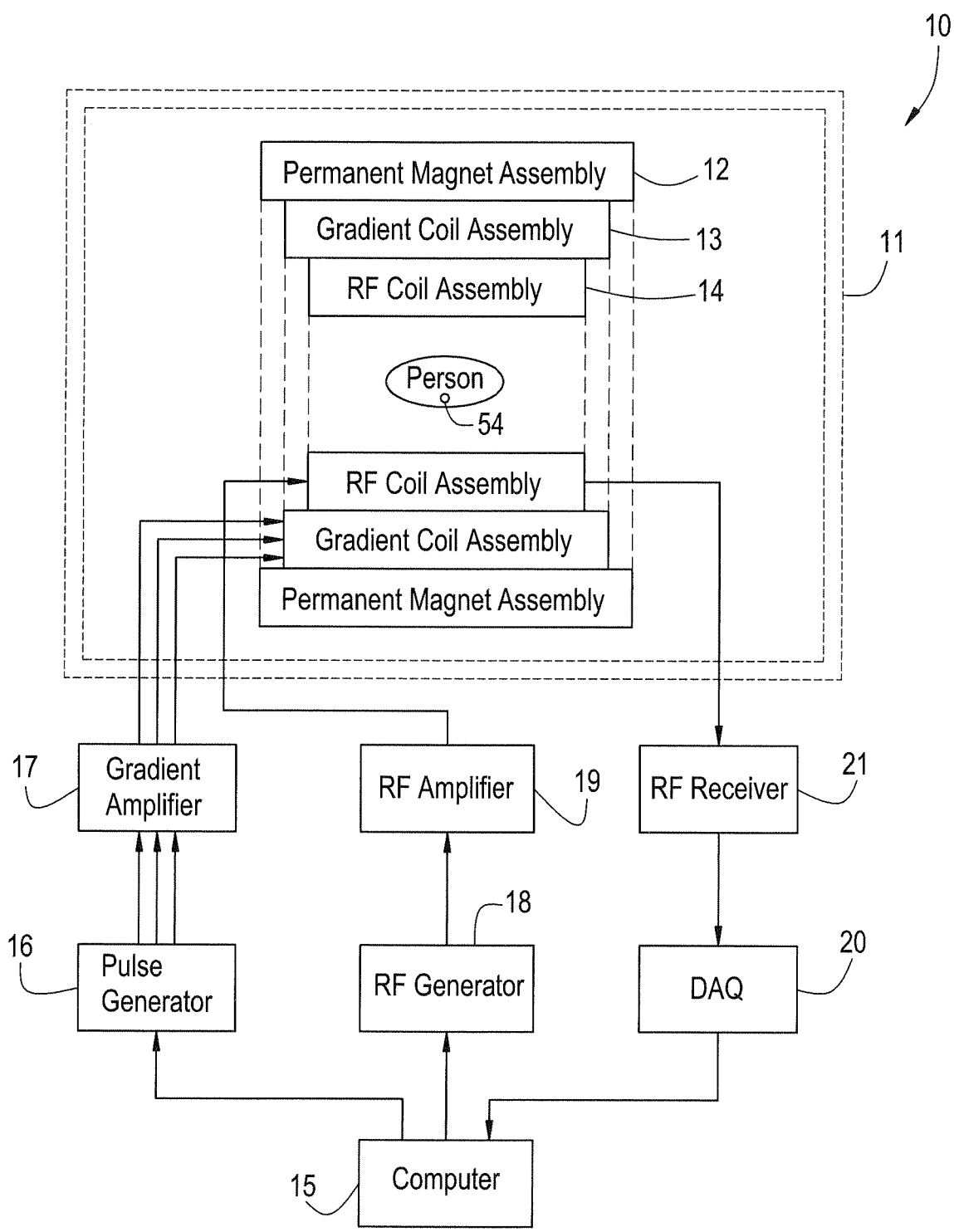
FIG. 1 is a schematic of an MRI scanning device.
Figure 2:
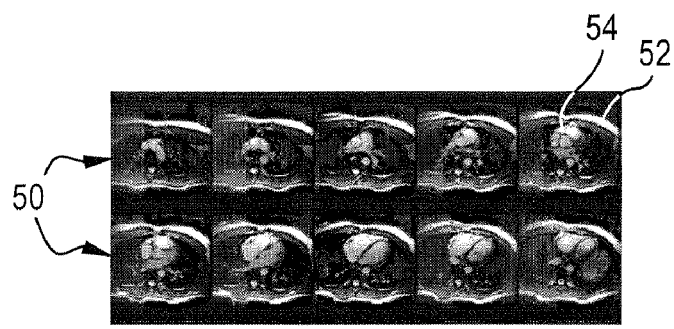
FIG. 2 is plurality of cross-sectional digital images of a heart.
Figure 3:
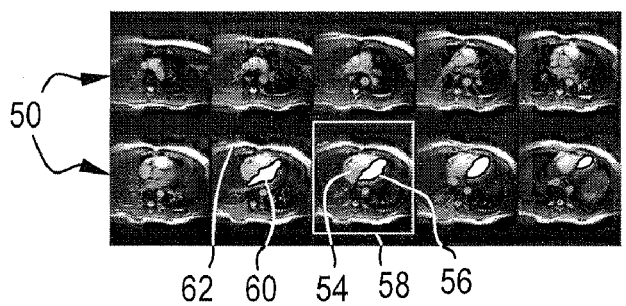
FIG. 3 is the plurality of cross-sectional digital images of FIG. 2 wherein a ventricular blood volume is illustrated.
Figure 4:
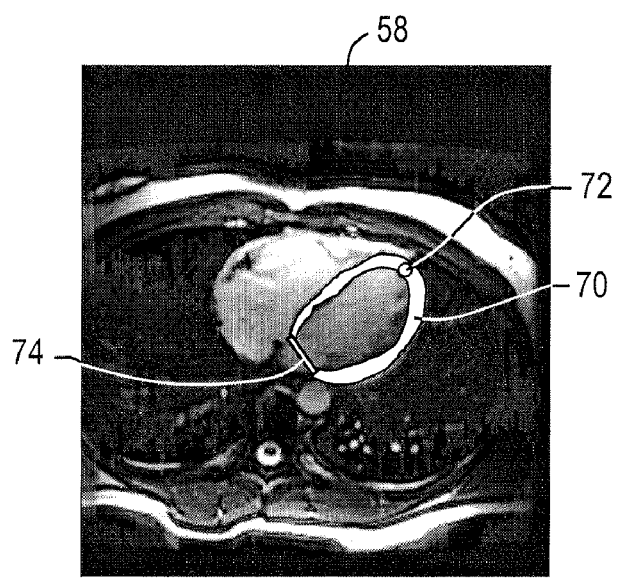
FIG. 4 is an enlarged view of a digital image of the heart obtained from one of the digital images of FIG. 3 wherein a left ventricular myocardium is illustrated.
Figure 5:
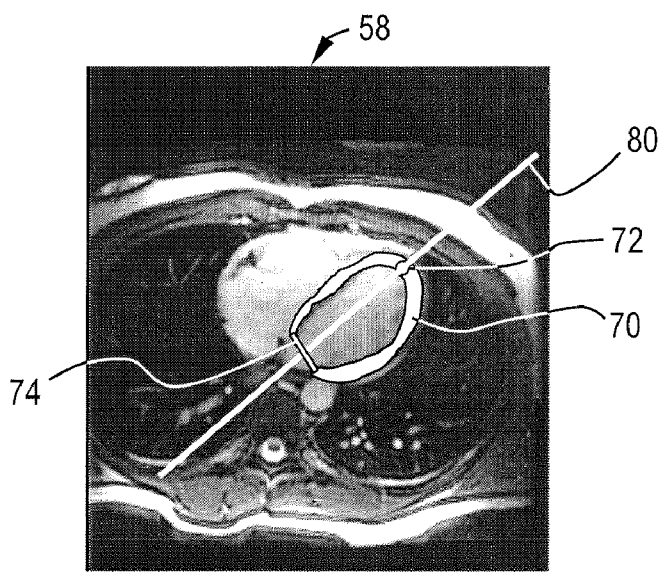
FIG. 5 is the digital image of FIG. 4 wherein a first axis is generated through the left ventricular myocardium.
Figure 6:
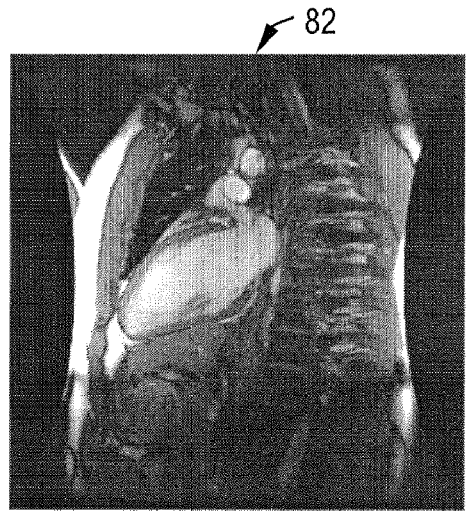
FIG. 6 is a digital image of the heart obtained by scanning an interior anatomy of a person along the first axis of FIG. 5.
Figure 7:
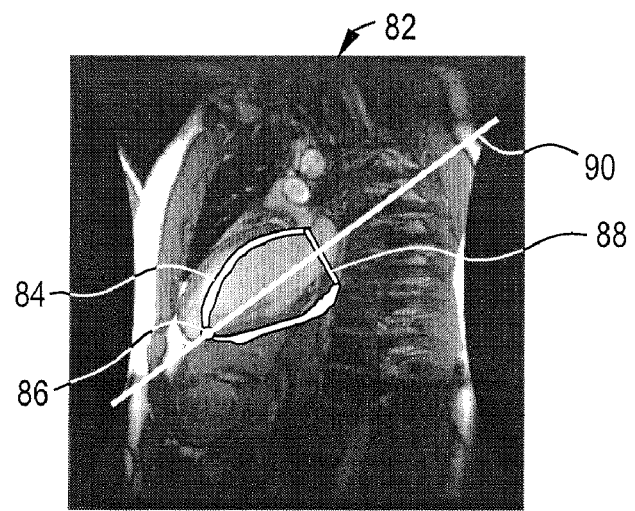
FIG. 7 is the digital image of FIG. 6 wherein a second axis is generated through the left ventricular myocardium.
Figure 8:
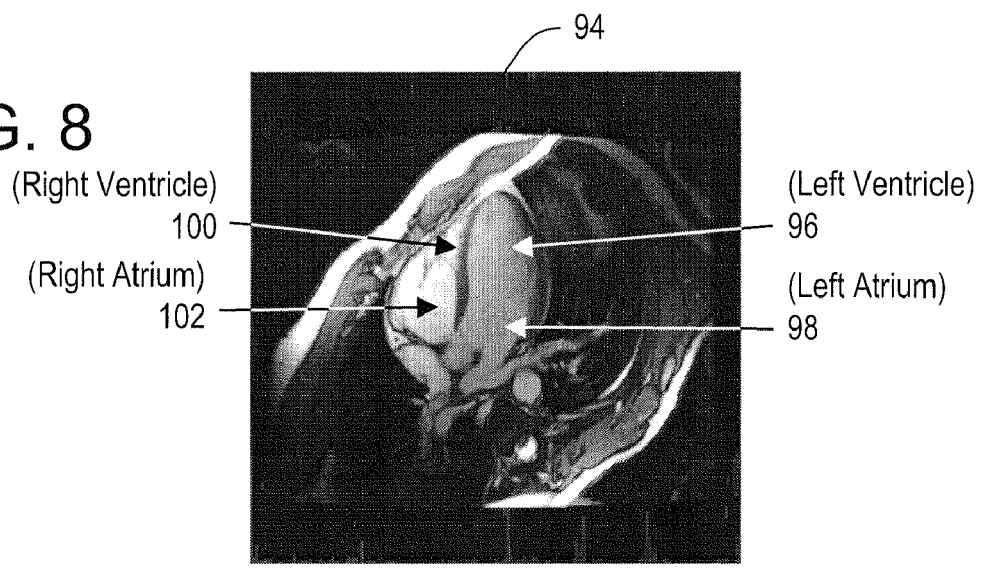
FIG. 8 is a digital image of the heart obtained by scanning an interior anatomy of a person along the second axis of FIG. 7.
Figure 9:
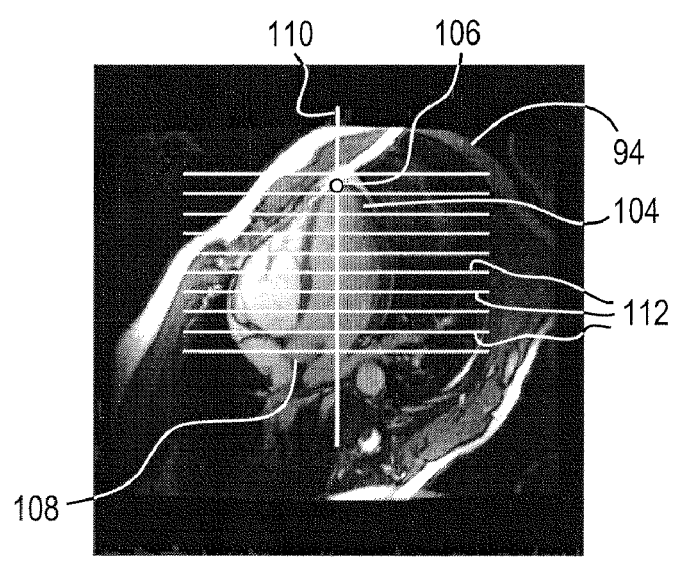
FIG. 9 is the digital image of FIG. 8 wherein a plurality of scanning planes is disposed in the digital image.
Figure 10:
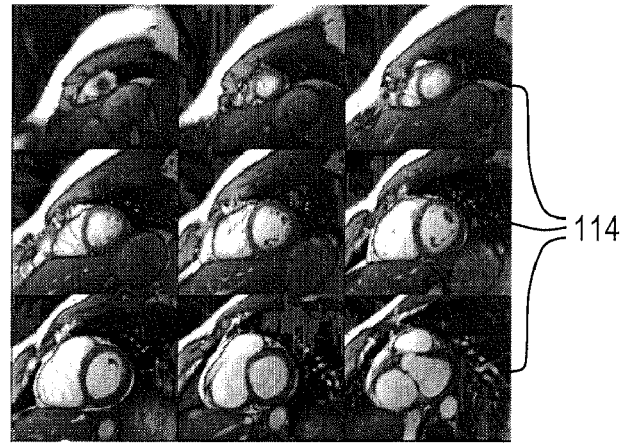
FIG. 10 is a plurality of 2-D digital images of the heart obtained by scanning interior anatomy of a person along the scanning planes of FIG. 9.
Figure 11:
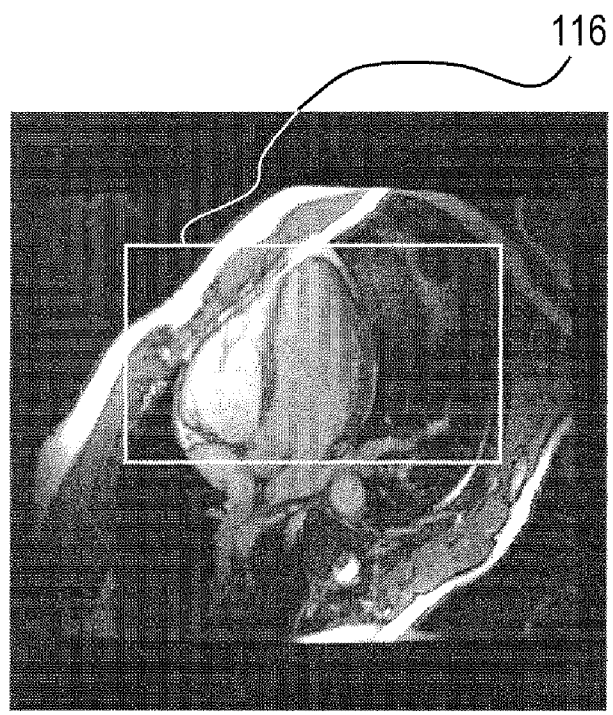
FIG. 11 is a 3-D digital image of the heart.
Figure 12:
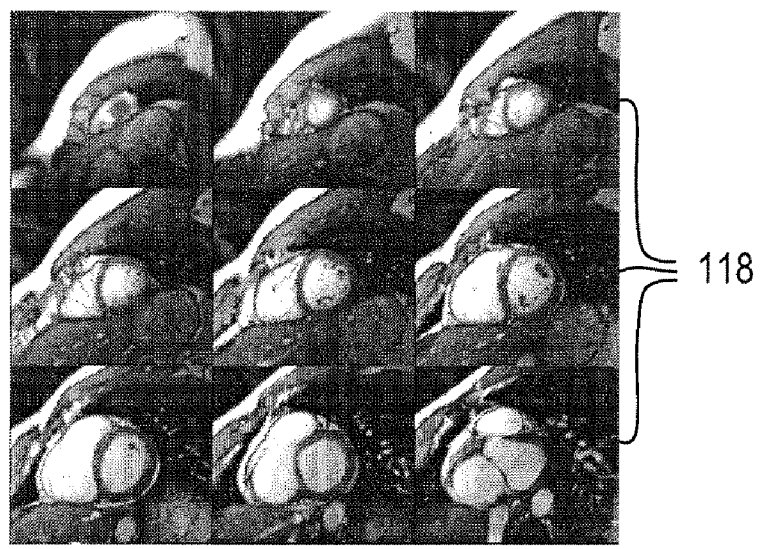
FIG. 12 is a plurality of 3-D digital images of the heart obtained from the 3-D digital image of FIG. 11.

Referring to FIGS. 1 and 2, an MRI scanning device 10 for generating digital images of a heart of a person in accordance with an exemplary embodiment is shown. The MRI imaging system 10 includes a housing 11, a permanent magnet assembly 12, a gradient coil assembly 13, an RF coil assembly 14, a computer 15, a pulse generator 16, a gradient amplifier 17, an RF generator 18, an RF amplifier 19, a data acquisition board 20, and an RF receiver 21.

The pulse generator 16 generates gradient signals that are amplified by the gradient amplifier 17 and transmitted to the gradient coil assembly 13, in response to a control signal received from the computer 15. In response, the gradient coil assembly 17 produces magnetic field gradients in the scanning region used for spatially encoding acquired signals.

The RF generator 18 generates signals that are amplified by the RF amplifier 19 and transmitted to the RF coil assembly 14, in response to a control signal being received from the computer 15. In response, the RF coil assembly 14 generates RF signals that propagate through a person in a scanning region and induces nuclei in predetermined regions of an internal anatomy of the person to emit RF signals that are received by the RF receiver 21. The received RF signals are digitized by the data acquisition board 20 and then transmitted to the computer 15.

The computer 15 is configured to generate 2-dimensional (2-D) digital images of an internal anatomy of a person, or 3-dimensional (3-D) digital images of the internal anatomy of the person, or both 2-D digital images and 3-D digital images, from the data received from the data acquisition board 20. In particular, the computer 15 is configured to allow a user to generate 2-D digital images of a human heart, or 3-D digital images of the human heart, or both 2-D digital images and 3-D digital images of the human heart.

Referring to FIGS. 13-15 and FIGS. 2-12, a method for automatically generating a digital image of a human heart in accordance with an exemplary embodiment is provided. The method can be implemented utilizing the system 10.

At step 140, the computer 15 induces the MRI scanning device 10 to scan an internal anatomy of a chest region 52 of the person to obtain first scanning data from the data acquisition board 20. In particular, the computer 15 induces the RF generator 18 to generate RF signals that propagate through a person in a scanning region to induce nuclei in the person to emit RF signals that are received by the RF receiver 21. Further, the computer induces the pulse generator 12 to generate gradient signals that are amplified by the gradient amplifier 17 and transmitted to the gradient coil assembly 13. The RF receiver 21 receives attenuated RF signals and generates output signals that are sampled by the data acquisition board 20. The data acquisition board 20 outputs sampled values, representing the first scanning data, to the computer 15.

At step 142, the computer 15 generates a plurality of cross-sectional digital images 50 of the heart 54 based on the first scanning data.

At step 144, the computer 15 automatically determines a ventricular blood volume 56 indicated by each of the plurality of cross-sectional digital images 50. In particular, the computer 15 utilizes region-growing techniques and imaging clustering techniques to determine a periphery of the ventricular blood volume 56.

At step 146, the computer 15 automatically selects a digital image 58 from the plurality of cross-sectional digital images 50 indicating a largest ventricular blood volume 56.

At step 148, the computer 15 automatically identifies a left ventricular myocardium 70 in the digital image 58 and both an apex position 72 and a base position 74 of the left ventricular myocardium 70 in the digital image 58. The computer 15 utilizes image-curvature techniques and image gradient techniques on the digital image 58 to determine the apex position 72. The base position 74 of the left ventricular myocardium 70 is obtained by generating a line between the two open-ended tips of the left ventricular myocardium 70.

At step 150, the computer 15 automatically generates an axis 80 extending through the apex position 72 and the base position 74 in the digital image 58.

At step 152, the computer 15 induces the MRI scanning device 10 to scan the internal anatomy of the chest region 52 of the person along the axis 80 perpendicular to a plane defined by the digital image 58 to obtain second scanning data from the data acquisition board 20.

At step 154, the computer 15 generates a digital image 82 of the heart 54 from the second scanning data.

At step 156, the computer 15 automatically identifies the left ventricular myocardium 84 in the digital image 82 and both an apex position 86 and a base position 88 of the left ventricular myocardium 84 in the digital image 82.

At step 158, the computer 15 automatically generates axis 90 extending through the apex position 86 and the base position 88 in the digital image 82.

At step 160, the computer 15 induces the MRI scanning device 10 to scan the internal anatomy of the chest region 52 of the person along a plane extending through the axis 90 and being perpendicular to a plane defined by the digital image 82 to obtain third scanning data from the data acquisition board 20. The axis 90 is referred to as a "true long axis" by those skilled in the art.

At step 162, the computer 15 generates a digital image 94 of four chambers of the heart 54 based on the third scanning data. In particular, the digital image 94 illustrates a left ventricle 96, a left atrium 98, a right ventricle 100, and a right atrium 102. The digital image 94 is referred to as a "four-chamber view" by those skilled in the art.

At step 164, the computer 15 automatically identifies the left ventricular myocardium 104 in the digital image 94 and both an apex position 106 and a base position 108 of the left ventricular myocardium 104 in the digital image 94.

At step 166, the computer 15 automatically generates an axis 110 extending through the apex position 106 and the base position 108 in the digital image 94.

At step 168, the computer 15 generates a plurality of planes 112 parallel to one another and perpendicular to both the axis 110 and to a plane defined by the digital image 94.

At step 170, the computer 15 makes a determination as to whether a user has selected to view a plurality of 2-D digital images of an internal anatomy of the person. If the value of step 170 equals "yes", the method advances to step 172. Otherwise, the method advances to step 176.

At step 172, the computer 15 induces the MRI scanning device 10 to scan an internal anatomy of the chest region 52 of the person along each of the plurality of planes 112 to obtain 2-D scanning data from the data acquisition board 20.

At step 174, the computer 15 generates a plurality of 2-D digital images 114 from the 2-D scanning data, wherein each of the 2-D digital images corresponds to an internal anatomy at one of the plurality of planes 112.

At step 176, the computer 15 makes a determination as to whether a user has selected to view a plurality of 3-D digital images of an internal anatomy of a person. If the value of step 176 equals "yes", the method advances to step 180. Otherwise, the method is exited.

At step 180, the computer 15 induces the MRI scanning device 10 to scan the internal anatomy of the chest region 52 of the person along each of the plurality of planes, similar to planes 112, in a scanning region 116 to obtain 3-D scanning data from the data acquisition board 20.

At step 182, the computer 15 generates a plurality of 3-D digital images 118 from the 3-D scanning data, wherein each of the 3-digital images corresponds to an internal anatomy proximate one of the plurality of planes in the scanning region 116.

The system and the method for automatically obtaining a digital image of a heart have substantial advantages over other systems and methods. In particular, the system and method have a technical effect of automatically obtaining a digital image of a heart. Thus, a desired digital image of the heart can be obtained with minimal intervention by a user of the MRI scanning device 10.

The method for automatically obtaining a digital image of a human heart can be embodied in the form of computer-implemented processes and apparatuses for practicing those processes. The method is embodied in computer program code executed in a computer. The present invention may be embodied in the form of computer program code containing instructions embodied in tangible media, such as floppy diskettes, CD-ROMs, hard drives, or any other computer-readable storage medium, wherein, when the computer program code is loaded into and executed by a computer, the computer becomes an apparatus for practicing the invention. The present invention can also be embodied in the form of computer program code, for example, whether stored in a storage medium, loaded into and/or executed by a computer, or transmitted over some transmission medium, such as over electrical wiring or cabling, through fiber optics, or via electromagnetic radiation, wherein, when the computer program code is loaded into and executed by a computer, the computer becomes an apparatus for practicing the invention. When implemented on a general-purpose microprocessor, the computer program code segments configure the microprocessor to obtain specific logic circuits.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed for carrying out this invention, but that the invention will include all embodiments falling within the scope of the appended claims. Moreover, the use of the terms first, second, etc. do not denote any order or importance, but rather the terms first, second, etc. are used to distinguish one element from another. Furthermore, the use of the terms a, an, etc. do not denote a limitation of quantity, but rather denote the presence of at least one of the referenced item.

We claim:

1. A method for obtaining a digital image of a heart of a person, comprising:

scanning an internal anatomy of a chest region of the person to obtain first scanning data;

generating a first plurality of cross-sectional digital images of the heart based on the first scanning data;

automatically determining a ventricular blood volume indicated by each of the first plurality of cross-sectional digital images;

automatically selecting a second digital image from the first plurality of cross-sectional digital images indicating a largest ventricular blood volume;

automatically identifying a left ventricular myocardium in the second digital image and both a first apex position and a first base position of the left ventricular myocardium in the second digital image;

automatically generating a first axis extending through the first apex position and the first base position in the second digital image;

scanning the internal anatomy of the chest region of the person along the first axis perpendicular to a first plane defined by the second digital image to obtain second scanning data;

generating a third digital image of the heart from the second scanning data;

automatically identifying the left ventricular myocardium in the third digital image and both a second apex position and a second base position of the left ventricular myocardium in the third digital image;

automatically generating a second axis extending through the second apex position and the second base position in the third digital image;

scanning the internal anatomy of the chest region of the person along a third plane extending through the second axis and being perpendicular to a second plane defined by the third digital image to obtain third scanning data; and generating a fourth digital image of four chambers of the heart based on the third scanning data.

2. The method of claim 1, further comprising:

automatically identifying the left ventricular myocardium in the fourth digital image and both a third apex position and a third base position of the left ventricular myocardium in the fourth digital image;

automatically generating a third axis extending through the third apex position and the third base position in the fourth digital image; and generating a first plurality of planes parallel to one another and perpendicular to both the third axis and to a fourth plane defined by the fourth digital image.

3. The method of claim 2, further comprising:

scanning the internal anatomy of the chest region of the person along each of the first plurality of planes to obtain 2-D scanning data; and generating a plurality of 2-D digital images from the 2-D scanning data, wherein each of the 2-D digital images corresponds to an internal anatomy at one of the first plurality of planes.

4. The method of claim 2, further comprising:

scanning the internal anatomy of the chest region of the person along each of the first plurality of planes to obtain 3-D scanning data; and generating a plurality of 3-D digital images from the 3-D scanning data, wherein each of the 3-digital images corresponds to an internal anatomy proximate one of the first plurality of planes.

5. A system for obtaining a digital image of a heart of a person, comprising:

an MRI scanning device configured to scan an internal anatomy of the person to obtain scanning data; and a computer operably coupled to the scanning device configured to generate cross-sectional digital images based on the scanning data, the computer is further configured to induce the scanning device to scan the internal anatomy of a chest region of the person to obtain first scanning data, the computer is further configured to generate a first plurality of cross-sectional digital images of the heart based on the first scanning data, the computer is further configured to automatically determine a ventricular blood volume indicated by each of the first plurality of cross-sectional digital images, the computer is further configured to automatically select a second digital image from the first plurality of cross-sectional digital images indicating a largest ventricular blood volume, the computer is further configured to automatically identify a left ventricular myocardium in the second digital image and both a first apex position and a first base position of the left ventricular myocardium in the second digital image, the computer is further configured to automatically generate a first axis extending through the first apex position and the first base position in the second digital image, the computer is further configured to scan the internal anatomy of the chest region of the person along the first axis perpendicular to a first plane defined by the second digital image to obtain second scanning data, the computer is further configured to generate a third digital image of the heart from the second scanning data, the computer is further configured to automatically identify the left ventricular myocardium in the third digital image and both a second apex position and a second base position of the left ventricular myocardium in the third digital image, the computer is further configured to automatically generate a second axis extending through the second apex position and the second base position in the third digital image, the computer is further configured to induce the scanning device to scan the internal anatomy of the chest region of the person along a third plane extending through the second axis and perpendicular to a second plane defined by the third digital image to obtain third scanning data, the computer is further configured to generate a fourth digital image of four chambers of the heart based on the third scanning data.

6. The system of claim 5, wherein the computer is further configured to automatically identify the left ventricular myocardium in the fourth digital image and both a third apex position and a third base position of the left ventricular myocardium in the fourth digital image, the computer is further configured to automatically generate a third axis extending through the third apex position and the third base position in the fourth digital image, the computer is further configured to generate a first plurality of planes parallel to one another and perpendicular to both the third axis and to a fourth plane defined by the fourth digital image.

7. The system of claim 6, wherein the computer is further configured to scan the internal anatomy of the chest region of the person along each of the first plurality of planes to obtain 2-D scanning data, the computer further configured to generate a plurality of 2-D digital images from the 2-D scanning data, wherein each of the 2-D digital images corresponds to an internal anatomy at one of the first plurality of planes.

8. The system of claim 6, wherein the computer is further configured to scan the internal anatomy of the chest region of the person along each of the first plurality of planes to obtain 3-D scanning data, the computer further configured to generate a plurality of 3-D digital images from the 3-D scanning data, wherein each of the 3-D digital images corresponds to an internal anatomy proximate one of the first plurality of planes.

9. An article of manufacture, comprising:

a computer storage medium having a computer program encoded therein for obtaining a digital image of a heart of a person, the computer storage medium comprising:

code for scanning an internal anatomy of a chest region of the person to obtain first scanning data;

code for generating a first plurality of cross-sectional digital images of the heart based on the first scanning data;

code for automatically determining a ventricular blood volume indicated by each of the first plurality of cross-sectional digital images;

code for automatically selecting a second digital image from the first plurality of cross-sectional digital images indicating a largest ventricular blood volume;

code for automatically identifying a left ventricular myocardium in the second digital image and both a first apex position and a first base position of the left ventricular myocardium in the second digital image;

code for automatically generating a first axis extending through the first apex position and the first base position in the second digital image;

code for scanning the internal anatomy of the chest region of the person along the first axis perpendicular to a first plane defined by the second digital image to obtain second scanning data;

code for generating a third digital image of the heart from the second scanning data;

code for automatically identifying the left ventricular myocardium in the third digital image and both a second apex position and a second base position of the left ventricular myocardium in the third digital image;

code for automatically generating a second axis extending through the second apex position and the second base position in the third digital image;

code for scanning the internal anatomy of the chest region of the person along a third plane extending through the second axis and perpendicular to a second plane defined by the third digital image to obtain third scanning data; and code for generating a fourth digital image of four chambers of the heart based on the third scanning data.

10. The article of manufacture of claim 9, wherein the computer storage medium further comprises:

code for automatically identifying the left ventricular myocardium in the fourth digital image and both a third apex position and a third base position of the left ventricular myocardium in the fourth digital image;

code for automatically generating a third axis extending through the third apex position and the third base position in the fourth digital image; and code for generating a first plurality of planes parallel to one another and perpendicular to both the third axis and to a fourth plane defined by the fourth digital image.

11. The article of manufacture of claim 10, wherein the computer storage medium further comprises:

code for scanning the internal anatomy of the chest region of the person along each of the first plurality of planes to obtain 2-D scanning data; and code for generating a plurality of 2-D digital images from the 2-D scanning data, wherein each of the 2-D digital images corresponds to an internal anatomy at one of the first plurality of planes.

12. The article of manufacture of claim 10, wherein the computer storage medium further comprises:

code for scanning the internal anatomy of the chest region of the person along each of the first plurality of planes to obtain 3-D scanning data; and code for generating a plurality of 3-D digital images from the 3-D scanning data, wherein each of the 3-digital images corresponds to an internal anatomy proximate one of the first plurality of planes.

* * * * *